United States Patent [19]

Hanefeld et al.

[11] Patent Number: 4,883,652
[45] Date of Patent: Nov. 28, 1989

[54] TETRAHYDRO-1,3,THIAZINE-2,4 DIONES, USE THEREOF AND SKIN TREATING COMPOSITIONS CONTAINING THEM

[75] Inventors: Wolfgang Hanefeld, Marburg, Fed. Rep. of Germany; Rudi Röthlisberger, Marly; Friedrich Noser, Bonnefontaine, both of Switzerland

[73] Assignee: Wella Aktiengesellschaft, Darmstadt, Fed. Rep. of Germany

[21] Appl. No.: 162,870

[22] Filed: Mar. 2, 1988

Related U.S. Application Data

[60] Division of Ser. No. 30,247, Mar. 24, 1987, Pat. No. 4,746,738, which is a continuation of Ser. No. 653,238, Sep. 7, 1984, abandoned.

[30] Foreign Application Priority Data

Feb. 12, 1983 [DE] Fed. Rep. of Germany ....... 3304871

[51] Int. Cl.$^4$ ................. A61K 7/40; A61K 7/42; A61K 7/48
[52] U.S. Cl. ........................... 424/59; 424/47; 424/63; 424/64; 514/844; 514/846; 514/847; 514/873; 514/938; 514/939
[58] Field of Search .......................... 424/59

[56] References Cited

U.S. PATENT DOCUMENTS 2,948,657  8/1960  Siccama ................. 424/59
3,781,418 12/1973  Poniot ................... 424/59

Primary Examiner—Dale R. Ore
Attorney, Agent, or Firm—Michael J. Striker

[57] ABSTRACT

Skin treating composition on the basis of compatible carrier and additional compositions with a content of a defined tetrahydro-1,3-thiazine-2,4-dion derivatives as active ingredients for thickening the epidermis. The skin treating compositions are applied 1-2 times daily onto the skin for about 3 to 4 weeks. Due to the thickening of the epidermis they cause a reinforcement of the skin, in particular against sun rays, cold and the contact with noxious environmental substances of all kinds. Moreover, the skin treating compositions are suitable for a prophylactic fighting of the so-called old age skin. An object of the invention are novel tetrahydro-1,3-thiazine-2,4-dion derivative which are active in the aforementioned manner having the formula

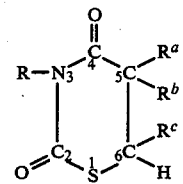

wherein R denotes H, alkyl, aryl, arylalkyl has substituted arylalkyl or substituted aryl in the aryl portion, $R^2$=H is aryl or substituted aryl, $R^b$=H, denotes aryl or substituted aryl and $R^3$=H, represents alkyl or aryl, provided that $R^a$, $R^b$ and $R^c$ only simultaneously denote H when R denotes a substituted arylalkyl in the aryl portion and R denotes H, but only if $R^a$=H$R^b$=aryl and $R^c$ constitute=H.

4 Claims, No Drawings

TETRAHYDRO-1,3,THIAZINE-2,4 DIONES, USE THEREOF AND SKIN TREATING COMPOSITIONS CONTAINING THEM

This is a division of application Ser. No. 030,247, filed Mar. 24, 1987, now U.S. Pat. No. 4,746,738, which is in turn a continuation of application Ser. No. 653,238, filed on Sept. 7, 1984, now abandoned.

The invention relates to tetrahydro-1,3 thiazine-2,4 dione as well as skin treating compositions containing the same.

The skin forms the limiting layer between the organism and its environment. Therefore, the most important task of the skin consists in protecting the inside of the body against external influences. Our skin is in daily contact with foreign matter which is partially hostile to the body and specifically to the skin. A frequent contact of the unprotected skin with these matters, which very often is caused by a profession (hairdressers, dentists, housewives) results in serious skin ages sooner or later. Hitherto, two different types of interventions were provided for preventing or at least for reducing these skin damages, namely by a protective skin protection as well as by a conserving skin care.

The protective skin care consists in that the skin is treated before coming in contact with the strange material, so as to substantially exclude the direct contact between the skin surface and the skin damaging materials. The preparations which assure a protective skin protection have a chemical-physical effect without interfering with the physiology of the skin. Such preparations must fulfill the following requirements: they should be impermeable and insoluble with respect to the most external noxegenics, they should have a good compatibility with the skin, they should be easy to apply and also easy to remove from the skin surface, they should not interfere with the touch of the hands and thereby not the operability and they should also provide a certain amount of durability. The disadvantage of known preparations of this type reside in that they are not able to fulfill these requirements in an optimum manner.

With the conserving skin care it is an object to make the skin less susceptible when coming into contact with skin damaging matters. The skin protecting materials are already contained in the washing agents. One makes a difference in their different types of skin protecting measures, that is, such which are effective by absorption of the skin surface, retroactive greasing measures, azidifying measures and synerisis measures. Here too, the essential disadvantage of these skin protecting measures consist in that they are not uniformly effective against all aggresions of the different environmental noxegenics.

In contrast thereto skin treatment compositions with a content of tetrahydro-1,3-thiazine-2,4-diodenes of the general formula I

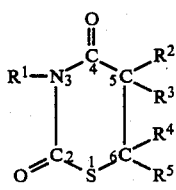

(I)

wherein
$R^1$ constitutes one of the residues H, alkyl, hydroxyalkyl, carboxyalkyl, halogenalkyl, cyanoalkyl, alkoxyalkyl, cycloalkyl, alkenyl, alkynyl, aryalkyl, substituted arylalkyl contained in the aryl constituent, aryl, alkyl-, halogen-, nitro-, alkoxy-, aryloxy-, cyano-substituted aryl, pyridil, thiazolyl, benzthiazolyl, thienyl, furyl, pyrazolyl, pyridazinyl, thiadiazolyl, pyrimidinyl and thiazinyl, $R^2$ and $R^3$ independent from each other mean H, halogen, alkyl, cycloalkyl, carboxyl, arylalkyl, aryl and substituted aryl, $R^4$ is one of the residues H, halogen, alkyl, halogenalkyl, carboxyalkyl, cycloalkyl, arylalkyl, aryl, substituted aryl, 2-furyl, substituted 2-furyl and that $R^5$ has the meaning of H, halogen, alkyl, cycloalkyl, arylalkyl, aryl and substituted aryl, fullfills all requirements which are asked for a skin treatment preparation in view of its novel effectiveness.

Therefore, the subject matter of the invention described herein relate to skin treatment compositions containing physiologically compatible support and additional compositions, characterized by at least one of the compounds of the general formula I.

The skin treatment compositions in accordance with the invention may be present in suitable prepared forms like, for example, as clear, dyed or turbid solution, as a dispersion, emulsion, in form of a foam or a preparation which can be sprayed from an aerosol container by means of a pump or a propellant gas. Preferably, they are present in form of an ointment, cream or gel. As examples for the preparations which are taken into consideration in accordance with the invention, particularly cosmetic skin treatment compositions are mentioned like day creams, night creams, nutrient creams, skin protection creams, sun protection creams, sun protection sprays, cold protection creams as well as lipsticks, skin milk preparations, skin lotions and skin protection gels.

The concentration of the compositions of general formula I is about 0,1 to 5% by weight, preferably 0,5 to 3% by weight in the skin treatment compositions. Thereby, the compositions of formula I may be present alone or in a mixture together with the remainder of the compositions.

The compound of the skin treatment compositions represents a mixture of the compounds in accordance with formula I with physiological compatible constituents which are customary for such preparations, like carrier and additional substances.

Customary carrier and additional substances in solutions, creams, emulsions or gels are solvents, for example, water, low aliphatic alcohols, for example, propanols, isopropanols or glycols, like glycerine and propylene glycol, furthermore wetting agents or emulsifiers from the classes of the anionic, cationic, amphoteric or noniogenic surface active substances like fatty alcohol sulfates, alkyl sulfonates, alkyl benzol sulfinates, alkyl trimethyl ammonium salts, alkylbetaine, oxethylized fatty alcohols, oxethylized nonylphenoles, fatty acid alkanolamides, oxethylized fatty acid esters, furthermore thickeners, like higher fatty alcohols, fatty acid esters, starches, cellulose derivatives, vaseline, stearine, ceresine, paraffine oil and fatty acids, as well as care substances, like lanoline, lanoline derivatives, cholesterine, panthotic acid, sorbite, betaine, almond oil, avocado oil, beeswax and spermaceti.

Further customary additional substances are, for example, cosmetic resins, dyes. perfume oils, propellant gases as well as conservation substances like, for example, p-hydroxybenoic acid, sorbic acid, salicic acid, formaldehyde and hexachlorophene. The compositions may contain bases for forming salt, for example, triethanolamine.

The making of the skin treatment compositions is performed in a manner customary for such preparations, in that the active ingredients of the compositions of formula I are admixed with the carrier substances for the skin treatment compositions and thereafter are further processed with the further constituents of the compositions until the product is finished. The compositions of the general formula I. The compositions of the general formula I mentioned as a constituent for the skin treatment composition described here, results in a thickening of the outer skin layer after a repeated epicutanic treatment, namely the dead callus layer which primarily is responsible for the natural skin protection. Due to the thickening of the callus layer the skin becomes more resistant against environmental noxious influences of all types, thus forming an optimum skin protection. Since the skin protection, which is provided by these compositions consist of reinforcing the natural skin protection, the skin protection in accordance with the invention containing the compositions in accordance with formula I does not possess the disadvantages which can be observed with conventional skin protection compositions. The skin treatment compositions can be applied onto the skin surface timely independent from the contact with the skin by the noxious substances. The skin treatment compositions in accordance with the invention can never interfere with an operating process because they are no longer present on the skin surface at this point in time. The skin protection can also not be removed (for example, by washing) since it is obtained by the new condition of the skin (thickening). Simultaneously, the compositions of general formula I result in a reinforcement of the natural sun protection. This additional sun protection is obtained by the thickening of the callus layer which is also obtained after the treatment with the skin treatment composition in accordance with the invention. A thickening of the callus layer results in an increased absorption of the light and sun. This novel prophylactic sun protection (pre-sun) has clear advantages with respect to the results obtained with conventional sun protection compositions. The customary sun protection compositions are applied onto the skin surface and therefore its absorption capacity, i.e., its light protection ability is dependent from the thickness of the layer applied. These preparations can interfere in that they give off too much fat, for example, thus soiling the clothing. For example, they are being rinsed off again by bathing or showering and must therefore be applied again. The comositions in accordance with the invention can be applied time independent from exposure to sun, in that it is applied epicutaneously and repeatedly 3 to 4 weeks before a summer vacation, for example, so that it offers a long lasting nonwashable protection from sunburn and other chronical light damages thanks to the thickened callus layer at the time of vacation.

The compositions in accordance with the invention afford a protection from cold on exposed and sensitive body locations, for example, the face and hands which are particularly exposed to rough weather conditions, due to its content of the tetrahydro-13-thiazine-2,4-diones of formula I. Therefore, these compositions are taken into consideration in particular for application by skiers and high mountain athletes, for example, as a preventive protection against extreme cold. Thanks to their callus layer thickening effect the skin treatment composition in accordance with the invention are able to offer an effective cold protection and which in this case also does not possess the uncomfortable side effects which are sensed with skin stressing preparations remaining on the skin surface, because this is merely a reinforcement of the natural cold protection.

With increasing age the outer layer of the skin the so-called upper skin or epidermis becomes thinner. The thinning of the epidermis is responsible that the skin surface assumes its typical parchment like appearance with age, so that sebaceous glands, retention zysts, pigment spots as well as fine blood vessels become visble, thus defining the typical condition of a so-called old skin. Since the compositions in accordance with the invention are not only able to thicken the callus layer of the skin, which represents only a part of the epidermis, but thickens the total epidermis it is an effective composition for a prophylactic treatment of skin aging.

The compositions in accordance with the invention are advantageously used in a manner in that they are applied repeatedly starting 3 to 4 weeks before a thickening of the callus or the epidermis should be present, and it should be preferably applied 1 to 2 times daily on the corresponding skin areas.

The skin thickening effect of the compositions in accordance with the invention was proven on hairless mice in the following manner:

The active ingredients were worked into suitable base substances and were epicutaneously applied during two and one half weeks, daily, except saturday and sunday on one body side of hairless mice (hr/hr). At the end of the treatment time the animals were killed, a roughly $1 \times 1.5$ cm skin face was removed and histologically prepared. The thickness of the upper skin was measured at about 100 locations and the average skin thickness was determined. The thickening of the upper skin was the result by the quotient of the average thickness of the treated upper skin and the average thickness of the untreated skin. This quotient is called the thickening factor. The compositions in accordance with the invention resulted in thickening factors between 1.3 and 2.2.

A number of the tetrahydro-1,3-thiazine-2,4-diones of the general formula I has been already made in accordance with different known processes. The processes are characterized in that they cannot be used universally. Unsubstituted compositions could only be obtained in position 5 and position 6 of the general formula I from N-monosubstituted thioncarbamide acetic esters by heating with $\beta$-halogen propionic esters[1,2] or $\beta$-propiolacton[3] in acetane hydride.

From thiourea and substituted 3-bromine propionic acids[4] or $\alpha$-substituted $\beta$-propiolactones[5] or substituted acrylic acids[6] unsubstituted compositions were obtained only on the ring nitrogen of the general formula I. From alkyl amines, carbon oxysulfide, alkali and $\beta$-propiolacton obtained 3-(carbamoylthio)-propionic acid after acidification were cycled to compositions of the general formula I, wherein $R^1$ could only be alkyl and the residues constituted $R^2$ to $R^5=H$[7].

Also the hitherto universal method for making compositions of the general formula I, whereby the compositions can be illustrated with alkyl- and alkyl residues in position 3, consisting in cycling N-alkyl- or aryl-substituted 3-(carbamoylthio)-propionic acid[8] results only in compositions with $R^2$ to $R^5$=H.

Also compositions of the general formula I were obtained with alkyl- or aryl residues in position 3 and the substitutes $R^2$ to $R^5$=H by oxidation of the corresponding tetrahydro-2-thioxo-1,3-thiazine-4-one with potassium dichromate in acetic acid or sulfuric acid solution[9]. It had been disadvantageous in the latter mentioned processes that the potassium dichromate is not sufficiently soluble even in the heat of the acetic acid reaction medium. If one adds water for improving the solubility, the poor water soluble tetrahydro-2-thioxo-1,3-thiazine-4-one are again precipitated and thereby partially removed from oxidation, so that the reaction is incomplete resulting in substance mixtures.

(1) N. A. Langlet, Ofversigt af kongl. (Svenska) Vetenskaps-Akademiens Förhandlinger 1892, page 166
(2) E. V. Vladzimirskaya, Zh. Obshch. Khim. 31, page 1921 (1961); C.A.55, 27328 (1961)
(3) W. Hanefeld, Justus Liebigs Ann. Chem. 1974, pages 2015-2018
(4) U.S. Pat. No. 2,585,064, K. W. Wheeler et al.
(5) British Pat. No. 1 007 587, G. Cignarella et al.
(6) K. Takemoto, H. Tahara, Y. Inaki, N. Ueda Chem. Lett. 1972, page 767
(7) E. Campaigne, P. K. Nargund J. Med. Chem. 7, (1964), page 132
(8) W. Hanefeld, Arch. Pharm. (Weinheim) 314, (1981), pages 315-328
(9) W. Hanefeld, Justus Liebigs Ann. Chem. 1974, pages 1789-1792

Compositions of the general formula II

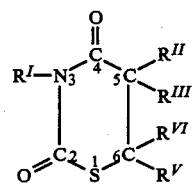
(II)

wherein
$R^I$ constitutes one of the residues H, alkyl, caboxyalkyl, halogen alkyl, alkoxyalkyl, cycloalkyl, arylalkyl, in the aryl portion substituted arylalkyl, aryl, alkyl-, halogen-, nitro-, alkoxy-, aryloxy-substituted aryl, pyrdyl, furyl, pyrazolyl, imidazolyl, pyridazinyl, pyrimidinyl and
$R^{II}$, $R^{III}$, $R^{IV}$ and $R^V$ denote independent from each other H, alkyl, cycloalkyl, arylalkyl, aryl and substituted aryl and can be made in that a tetrahydro-2-thioxo-1,3-thiazine-4-on of the general formula

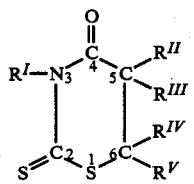

whereby the substitutes $R^I$, $R^{II}$, $R^{III}$, $R^{IV}$ and $R^V$ have the aforementioned meaning, whereby the composition is heated for one hour to a boiling point in acetic acid with the triple molar amount of chromic acid anhydride ($CrO_3$), thereafter the reaction mixture is compounded with water and after cooling off the generated tetrahydro-1,3-thiazine-2,4-dion of the formula II it isolated from the reaction mixture.

The illustration of the compositions in accordance with formula II is performed in a homogenic solution in this process, since $CrO_3$ dissolves completely in acetic acid under the used concentration conditions. Thereby, the aforementioned difficulties when operating with potassium dichromate as the oxidation composition are avoided. This process permits for the first time the illustration of substituted compositions on $C_5$ and/or $C_6$ of general formula II with a simultaneous substitution at $N_3$.

Therefore, the subject application relates to further particularly suitable tetrahydro-1,3-thiazine-2,4-diones of the general formula III for use in the skin treatment compositions in accordance with the invention

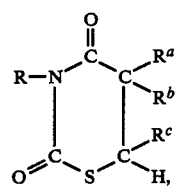
(III)

wherein R denotes H, alkyl, aryl, arylalkyl has substituted arylalkyl or substituted aryl in the aryl portion, $R^a$=H is aryl or substituted aryl, $R^b$=H, denotes aryl or substituted aryl and $R^c$=H, represents alkyl or aryl, provided that $R^a$, $R^b$ and $R^c$ only simultaneously denote H when R denotes a substituted arylalkyl in the aryl portion and R denotes H, but only if $R^a$=$R^b$=aryl and $R^c$ constitute=H.

Examples for composition in accordance with the invention according to formula III are:
(a) 3-(4-chlorbenzyl)-tetrahydro-1,3-thiazine-2,4-dione
(b) 3-(4-chlorphenyl)-6-methyl-tetrahydro-1,3-thiazine-2,4-dion
(c) 3-benzyl-6-methyl-tetrahydro-1,3-thiazine-2,4-dione
(d) 6-methyl-3-(2-phenylethyl)-tetrahydro-1,3-thiazine-2,4-dion
(e) 5,5-diphenyl-tetrahydro-1,3-thiazine-2,4-dione
(f) 3-methyl-5,5-diphenyl-tetrahydro-1,3-thiazine-2,4-dione
(g) 6-phenyl-3-(4-methoxyphenyl)-tetrahydro-1,3-thiazine-2,4-dion
(h) 6-phenyl-3-(2-phenylethyl)-tetrahydro-1,3-thiazine-2,4-dione
(i) 3-ethyl-5,5-diphenyl-tetrahydro-1,3-thiazine-2,4-dione
(j) 3-methyl-5,5-di-(4-tolyl)-tetrahydro-1,3-thiazine-2,4-dione
(k) 3-(4-chlorphenyl)-5,5-diphenyl-tetrahydro-1,3-thiazine-2,4-dione
(l) 3,5,5-triphenyl-tetrahydro-1,3-thiazine-2,4-dione
(m) 3-(4-chlorbenzyl)-5,6-diphenyl-tetrahydro-1,3-thiazine-2,4-dione
(n) 3-benzyl-5,5-diphenyl-tetrahydro-1,3-thiazine-2,4-dione
(o) 3-benzyl-5,5-di-(4-tolyl)-tetrahydro-1,3-thiazine-2,4-dione The following example should explain the subject matter of the invention more clearly:

EXAMPLES FOR SKIN TREATMENT COMPOSITIONS

Preparation for skin protection
Cream
- 2,0 g  3-benzyl-tetrahydro-1,3-thiazine-2,4-dione
- 6,0 g  mixture from 60% by weight glycerine monostearate and 40% by weight glycerine distearate
- 4,0 g  polyoxyethylene glycerine monostearate
- 3,0 g  cetylalcohol
- 2,0 g  paraffine oil, thick liquid
- 1,0 g  lanoline
- 0,3 g  perfume and conservation composition
- 81,7 g water
- 100,0 g

Lotion
- 1,5 g  3-phenyl-tetrahydrol-1,3-thiazine-2,4-dione
- 0,5 g  isopropyl-lanolate
- 3,0 g  stearic acid, pressed three times
- 2,0 g  glycerine monostearate
- 1,0 g  triethanolamin
- 0,3 g  perfume and conservation composition
- 91,7 g water
- 100,0 g

Pre-sun-preparations (sun protection compositions)
Milk
- 2,5 g  tetrahydro-1,3-thiazine-2,4-dione
- 3,0 g  cetyl phosphoric acid-diethanolamine salt
- 3,0 g  stearinic acid, three times pressed
- 5,0 g  isopropyl palmitate
- 5,0 g  paraffine oil, thin liquid
- 0,5 g  perfume and conservation composition
- 81,0 g water
- 100,0 g

Body lotion
- 2,0 g  3-benzyl-5,5-diphenyl-tetrahydro-1,3-thiazine-2,4-dione
- 6,6 g  propylene glycol-mono-and distearate, not self-emulsifying (monostearate content 60%)
- 1,4 g  triethanolamine
- 1,0 g  lanolin
- 2,0 g  isopropylmyristate
- 2,0 g  2-octyldodecanol
- 5,0 g  avacado oil
- 2,6 g  starinic acid, three times pressed
- 0,6 g  oleic acid
- 3,0 g  sorbite
- 0,5 g  perfume and conversation composition
- 73,3 g water
- 100,0 g

Preparations for the prophylactic cold protection
Cream
- 5,0 g  3-benzyl-tetrahydro-1,3-thiazine-2,4-dione
- 12,0 g glycerine monostearate, self emulsifying
- 10,0 g isocetyl stearate
- 0,3 g  perfume and conservation compositions
- 72,7 g water
- 100,0 g

Emulsion
- 2,0 g  5,5-diphenyl-tetrahydro-1,3-thiazin-2,4-dione
- 7,0 g  glycerine monostearate
- 3,0 g  cetyl stearyl alcohol
- 10,0 g oleic acid decylester
- 10,0 g isopropylmyristate
- 0,5 g  perfume and conversation compositions
- 67,5 g water
- 100,0 g

Preparations for the prophylactic treatment of old age skin
Night cream
- 1,5 g  3-(4-chlorbenzyl)-tetrahydro-1,3-thiazine-2,4-dione
- 22,0 g lanolin alcohol fractions
- 5,0 g  isopropylmyristate
- 3,0 g  ceresine (paraffinum solidum)
- 3,0 g  lanoline
- 5,0 g  glycerine
- 0,5 g  perfume and conservation compositions
- 60,0 g water
- 100,0 g

Face and neck cream
- 2,0 g  3-phenyl-tetrahydro-1,3-thiazine-2,4-dione
- 3,0 g  cethyl phosphoric acid-diethanolamine salt
- 5,0 g  stearic acid, three times pressed
- 15,3 g almond oil
- 10,0 g isopropyl palmitate
- 5,0 g  lanolin
- 0,6 g  perfume and conservation compositions
- 59,1 g water
- 100,0 g

Manufacturing Examples

Making of 3 methyl-5,5-diphenyl-tetrahydro-1,3-thiazine-2,4-dione (f): 13,5 g (0,043 Mol) 3-methyl-5,5-diphenyl-2-thioxo-tetra-hydro-1,3-thiazine-4-on and 18,0 g (0,18 Mol) chromic acid anhydride are heated to a boiling for 1 hour in 100 g acetic acid. One compounds with water up to the beginning of turbidity and cooling off. The precipitated crystals are suctioned off, washed with water, dried and recrystalyzed from toluol/petrol ether. The physical data and and analysis values can be seen from the following table.

For the remainder of the compositions in accordance with general formula III listed in the following table (compositions a–e and g–o), the illustration for the corresponding 2-thioxo compound in analog manner as described above for the composition (f). However, as a solvent for the recrystallisation one may use diluted acetic acid chloroform/petrol ether or ethanol/H$_2$O, depending on the substance (see table). The volume of the individual charges were between 1 and 50 mMol.

TABLE
Inventive tetrahydro-1,3-thiazine-2,4-diones of the general formula III

| | R | $R^a$ | $R^b$ | $R^c$ | Melting point °C. (recrystallisation from) | Yield % of the theory | Sum formula (Mol amount) | Analysis N calculated found | S | Cl |
|---|---|---|---|---|---|---|---|---|---|---|
| a | 4-Cl—C$_6$—CH$_2$ | H | H | H | 72–74,5 (diluted acetic acid) | 50 | C$_{11}$H$_{10}$ClNO$_2$S (255.7) | 5.48 / 5.32 | 12.54 / 12.46 | 13,87 / 13.87 |
| b | 4-Cl—C$_6$H$_4$ | H | H | CH$_3$ | 128–130 (diluted acetic acid) | 26 | C$_{11}$H$_{10}$ClNO$_2$S (255.7) | 5.48 / 5.55 | 12.54 / 12.79 | |
| c | C$_6$H$_5$—CH$_2$ | H | H | CH$_3$ | 68–70 | 27 | C$_{12}$H$_{13}$NO$_2$S | 5.95 | 13.63 | |

TABLE-continued
Inventive tetrahydro-1,3-thiazine-2,4-diones of the general formula III

| | R | $R^a$ | $R^b$ | $R^c$ | Melting point °C. (recrystallisation from) | Yield % of the theory | Sum formula (Mol amount) | N calculated found | S calculated found | Cl |
|---|---|---|---|---|---|---|---|---|---|---|
| | | | | | (diluted acetic acid) | | (253.3) | 5.94 | 13.34 | |
| d | $C_6H_5$—$CH_2$—$CH_2$ | H | H | $CH_3$ | 113–115,5 | 64 | $C_{13}H_{15}NO_2S$ | 5.62 | 12.86 | |
| | | | | | (toluol/petrolether) | | (249,3) | 5,38 | 12.83 | |
| e | H | $C_6H_5$ | $C_6H_5$ | H | 181–183 | 70 | $C_{16}H_{13}NO_2S$ | 4.94 | 11.32 | |
| | | | | | (chloroform/petrol = ether) | | (283,4) | 4,86 | 11.38 | |
| f | $CH_3$ | $C_6H_5$ | $C_6H_5$ | H | 146 | 52 | $C_{17}H_{15}NO_2S$ | 4.71 | 10.78 | |
| | | | | | (toluol/petrolether) | | (297.4) | 4,63 | 11.14 | |
| g | 4-$CH_3O$—$C_6H_4$ | H | H | $C_6H_5$ | 203–205 | 50 | $C_{17}H_{15}NO_3S$ | 4.47 | 10.23 | |
| | | | | | (toluol/ethanol) | | (313,4) | | | |
| h | $C_6H_5$—$CH_2$—$CH_2$ | H | H | $C_6H_5$ | 132–134 | 72 | $C_{18}H_{17}NO_2S$ | 4.50 | 10.30 | |
| | | | | | (ethanol/$H_2O$) | | (311,4) | 4.50 | 10.29 | |
| i | $C_2H_5$ | $C_6H_5$ | $C_6H_5$ | H | 139–141 | 67 | $C_{18}H_{17}NO_2S$ | 4,50 | 10.30 | |
| | | | | | (ether) | | (311.4) | 4.52 | 10.25 | |
| j | $CH_3$ | 4-$CH_3C_6H_4$ | 4-$CH_3$—$C_6H_4$ | H | 175–176 | 32 | $C_{19}H_{19}NO_2S$ | 4.30 | 9.85 | |
| | | | | | (diluted acetic acid) | | (325.4) | 4.10 | 10.20 | |
| k | 4-Cl—$C_6H_4$ | $C_6H_5$ | $C_6H_5$ | H | 171–175 | 74 | $C_{22}H_{16}ClNO_2S$ | 3.56 | 8.14 | |
| | | | | | (diluted acetic acid) | | (393,9) | 3.54 | 7.82 | |
| l | $C_6H_5$ | $C_6H_5$ | $C_6H_5$ | H | 167–169 | 68 | $C_{22}H_{17}NO_2S$ | 3.90 | 8.92 | |
| | | | | | (ethanol/petrol ether) | | (359,5) | 3.88 | 8.96 | |
| m | 4-Cl—$C_6H_4$—$CH_2$ | H | $C_6H_5$ | $C_6H_5$ | 149–150,5 | 70 | $C_{23}H_{18}ClNO_2S$ | 3.43 | 7.86 | 8.69 |
| | | | | | (toluol/petrolether) | 70 | (407,9) | 3.39 | 7.91 | 8.40 |
| n | $C_6H_5$—$CH_2$ | $C_6H_5$ | $C_6H_5$ | H | (181–182) | 64 | $C_{23}H_{19}NO_2S$ | 3.75 | 8.59 | |
| | | | | | (toluol/petrol ether) | | (373,5) | 3.50 | 8.53 | |
| o | $C_6H_5$—$CH_2$ | 4-$Cl_3$—$C_6H_4$ | 4-$CH_3$—$C_6H_4$ | H | 177–180 | 60 | $C_{25}H_{23}NO_2S$ | 3.49 | 7.99 | |
| | | | | | (diluted acetic acid) | | (401,5) | 3.20 | 7.99 | |

In the infrared spectrum the compositions in accordance with the invention show a carbamoyl-C-O-oscillation of the $C_2$ at 1630–1670 cm$^{-1}$ and a lactam-C-O-oscillation of the $C_4$ at 1700–1720 cm$^{-1}$. In addition, the composition (e) shows a NH-band at 3320 cm$^{-1}$.

We claim:

1. A cosmetic skin treatment composition comprising, in a physiologically compatible cosmetic carrier, an effective amount of at least one tetrahydro-1,3-thiazine-2,4-dione of the general formula (I)

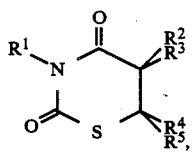

wherein $R^1$ represents H, alkyl (C1–C4), phenyl, phenyl alkyl (C1–C4), phenyl substituted in para positioning with alkyl (C1–C4), halogen, nitro, alkoxy (C1–C4), phenyloxy or cyano, phenyl alkyl (C1–C4) substituted in para positioning in the phenyl moiety with alkyl (C1–C4), halogen, nitro, alkoxy (C1–C4), phenyloxy or cyano, $R^2$ and $R^3$ are independently H, phenyl, phenyl substituted in para positioning with alkyl (C1–C4), halogen, nitro, alkoxy (C1–C4), phenyloxy or cyano, $R^4$ and $R^5$ are independently H, alkyl (C1–C4) or phenyl.

2. The composition according to claim 1, characterized in that the compounds of formula (I) are contained in an amount of 0.1 to 5% by weight.

3. The composition according to claim 1, characterized in that the compounds of formula (I) are contained in an amount of 0.1 to 3% by weight.

4. The composition according to claim 1, characterized in that the compounds of formula (I) are selected from the group consisting of 3-benzyl-tetrahydro-1,3-thiazine-2,4-dione,
3-phenyl-tetrahydro-1,3-thiazine-2,4-dione,
tetrahydro-1,3-thiazine-2,4-dione,
3-(4-chlorobenzyl)-tetrahydro-1,3-thiazine-2,4-dione,
3-(4-chlorophenyl)-6-methyl-tetrahydro-1,3-thiazine-2,4-dione,
3-benzyl-6-methyl-tetrahydro-1,3-thiazine-2,4-dione,
6-methyl-3-(2-phenylethyl)-tetrahydro-1,3-thiazine-2,4-dione,
5,5-diphenyl-tetrahydro-1,3-thiazine-2,4-dione,
3-methyl-5,5-diphenyl-tetrahydro-1,3-thiazine-2,4-dione,
6-phenyl-3-(4-methoxyphenyl)-tetrahydro-1,3-thiazine-2,4-dione,
6-phenyl-3-(2-phenylethyl)-tetrahydro-1,3-thiazine-2,4-dione,
3-ethyl-5,5-diphenyl-tetrahydro-1,3-thiazine-2,4-dione,
3-methyl-5,5-di-(4-tolyl)-tetrahydro-1,3-thiazine-2,4-dione,
3-(4-chlorophenyl)-5,5-diphenyl-tetrahydro-1,3-thiazine-2,4-dione,
3,5,5-triphenyl-tetrahydro-1,3-thiazine-2,4-dione,
3-(4-chlorobenzyl)-5,6-diphenyl-tetrahydro-1,3-thiazine-2,4-dione,
3-benzyl-5,5-diphenyl-tetrahydro-1,3-thiazine-2,4-dione and
3-benzyl-5,5-di-(4-tolyl)-tetrahydro-1,3-thiazine-2,4-dione.

* * * * *